(12) United States Patent
Haddad

(10) Patent No.: US 12,718,910 B2
(45) Date of Patent: Aug. 25, 2026

(54) COMPUTER SYSTEM AND METHOD FOR DETERMINING CANDIDATES FOR INCLUSION WITHIN A COHORT

(71) Applicant: Tempus AI, Inc., Chicago, IL (US)

(72) Inventor: Dany Michael Haddad, Austin, TX (US)

(73) Assignee: Tempus AI, Inc., Chicago, IL (US)

( * ) Notice: Subject to any disclaimer, the term of this patent is extended or adjusted under 35 U.S.C. 154(b) by 455 days.

(21) Appl. No.: 18/162,097

(22) Filed: Jan. 31, 2023

(65) Prior Publication Data

US 2023/0352124 A1 Nov. 2, 2023

Related U.S. Application Data

(60) Provisional application No. 63/336,100, filed on Apr. 28, 2022.

(51) Int. Cl.
*G16H 10/20* (2018.01)
*G16H 10/60* (2018.01)
*G16H 50/20* (2018.01)
*G16H 50/70* (2018.01)

(52) U.S. Cl.
CPC ............. *G16H 10/20* (2018.01); *G16H 10/60* (2018.01); *G16H 50/20* (2018.01); *G16H 50/70* (2018.01)

(58) Field of Classification Search
None
See application file for complete search history.

(56) References Cited

U.S. PATENT DOCUMENTS

| | | | | |
|---|---|---|---|---|
| 11,328,796 | B1 * | 5/2022 | Jain | G16H 10/20 |
| 2019/0304575 | A1 * | 10/2019 | Beltre | G16H 40/20 |
| 2019/0311787 | A1 * | 10/2019 | Graiver | G16H 10/60 |
| 2020/0043612 | A1 * | 2/2020 | McNair | G16H 50/30 |
| 2020/0243167 | A1 * | 7/2020 | Will | G06N 20/20 |

OTHER PUBLICATIONS

Alexander et al. ("Evaluation of an artificial intelligence clinical trial matching system in Australian lung cancer patients," JAMIA Open, vol. 3, Issue 2, Jul. 2020, pp. 209-215) (Year: 2020).*

(Continued)

*Primary Examiner* — Christopher B Tokarczyk
(74) *Attorney, Agent, or Firm* — MORGAN, LEWIS & BOCKIUS LLP

(57) ABSTRACT

A computer system receives, from a user, a set of clinical eligibility criteria. The computer system retrieves, from a database, medical records for a plurality of subjects. The computer system inputs, into a model comprising 1000 parameters: information corresponding to the set of clinical eligibility criteria; and information corresponding to the medical records for at least a first subset of the plurality of subjects. The computer system receives, from the model, responsive to the inputting, a ranking of the first subset of the plurality of subjects indicative of relative relevance of the respective medical histories of the plurality of subjects to the set of clinical eligibility criteria. The computer system selects, based on the ranking, a second subset of the plurality of subjects for inclusion in the cohort.

18 Claims, 7 Drawing Sheets

(56) References Cited

OTHER PUBLICATIONS

MatchMiner: An open-source platform for cancer precision medicine, npj Precision Oncology, 2022, https://matchminer.org/, pp. 1-10.
Abualsaud, Mustafa et al. "A System for Efficient High-Recall Retrieval," Proceedings of the 41st International ACM SIGIR Conference on Research and Development in Information Retrieval (SIGIR 2018), pp. 1-4.
Kaskovich, Samuel et al., 2023, "Automated Matching of Patients to Clinical Trials: A Patient-Centric Natural Language Processing Approach for Pediatric Leukemia," ASCO, JCO Clinical Cancer Informatics, pp. 1-9.
Klein, Harry et al. "MatchMiner: an open-source platform for cancer precision Medicine," Precision Oncology (2022) 69, pp. 1-9.
Zamani, Hamed et al., "On the Theory ofWeak Supervision for Information Retrieval," ICTIR'18, Sep. 14-17, 2018, Long Paper Session 6: Theory of Models, pp. 147-154.

* cited by examiner

COMPUTER SYSTEM AND METHOD FOR DETERMINING CANDIDATES FOR INCLUSION WITHIN A COHORT

PRIORITY APPLICATION

This application claims priority to U.S. Prov. App No. 63/336,100, filed Apr. 28, 2022, which is hereby incorporated by reference in its entirety.

TECHNICAL FIELD

The present invention generally relates to generating candidate subjects (e.g., human subjects) for inclusion within a cohort (e.g., for the purposes of a study), and more particularly to a computer system that ranks subjects based on the relevance of their unstructured medical records to a set of clinical eligibility criteria.

BACKGROUND

It is frequently important in medical research to reliably identify cohorts of subjects (e.g., human subjects) that meet particular clinical eligibility criteria. For example, when testing a new pharmaceutical drug on patients that have previously been treated with a specific prior drug, it is critical to be able to identify patients who have been treated with that particular prior drug.

Electronic Health Records (EHR) provide a valuable source of information with which to identify such subjects, but electronic health records also give rise to certain challenges in cohort identification. Such challenges often result from the fact that electronic health records are not typically designed for cohort identification, but rather to communicate important patient care information between healthcare providers. As such, electronic health records frequently contain unstructured text, such as doctors' chart notes, containing information that is difficult for computer-based categorization. For example, a chart note may include a suggestion that a particular drug be considered at a later time, or may state that the particular drug was administered under the doctor's care. The latter case would lead to inclusion within a cohort of individuals who have received the particular drug, whereas the former would not.

SUMMARY

To address these problems, a method of determining a cohort for a study (e.g., identifying candidates for inclusion within the cohort) is provided. The method includes receiving, from a user, a set of clinical eligibility criteria. The method further includes retrieving, from a database, medical records for a plurality of subjects. The method further includes inputting, into a model comprising 1000 parameters: information corresponding to the set of clinical eligibility criteria; and information corresponding to the medical records for at least a first subset of the plurality of subjects. The method further includes receiving, from the model, responsive to the inputting, a ranking of the first subset of the plurality of subjects indicative of relative relevance of the respective medical histories of the plurality of subjects to the set of clinical eligibility criteria. The method further includes selecting, based on the ranking, a second subset of the plurality of subjects for inclusion in the cohort.

In accordance with some embodiments, a computer system is provided. The electronic device includes one or more processors and memory storing one or more programs. The one or more programs include instructions for performing any of the methods described herein.

In accordance with some embodiments, a non-transitory computer-readable storage medium is provided. The non-transitory computer-readable storage medium stores one or more programs for execution by a computer system with one or more processors. The one or more programs include instructions for performing any of the methods described herein.

Thus, systems are provided with improved methods for generating candidates for inclusion within a cohort based on clinical eligibility criteria.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings and specification.

DETAILED DESCRIPTION

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known components have not been described in detail so as not to unnecessarily obscure aspects of the embodiments.

It will also be understood that, although the terms first, second, etc., are, in some instances, used herein to describe various elements, these elements should not be limited by these terms. These terms are used only to distinguish one element from another. For example, a first encoder could be termed a second encoder, and, similarly, a second encoder could be termed a first encoder, without departing from the scope of the various described embodiments. The first encoder and the second encoder are both encoders, but they are not the same encoder.

The terminology used in the description of the various embodiments described herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

Figure 1:
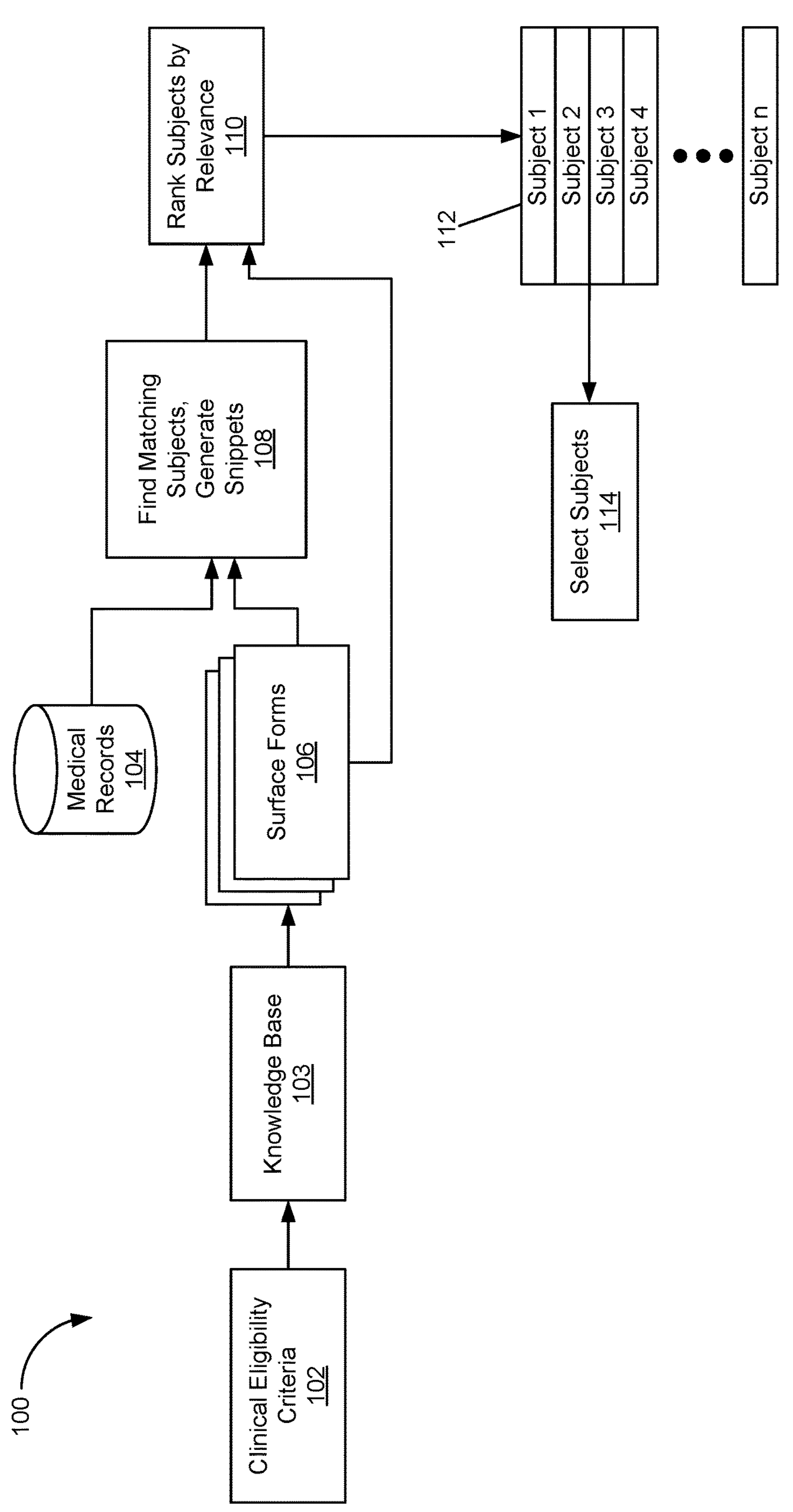
FIG. 1 is a schematic diagram of a system for determining candidates for inclusion within a cohort (e.g., generating candidates for inclusion within the cohort), in accordance with some embodiments.

FIG. 1 is a schematic diagram of a system 100 for determining candidates for inclusion within a cohort (e.g., generating candidates for inclusion within the cohort), in accordance with some embodiments. The system 100 includes a user interface, which receives, from a user (e.g., a researcher looking to generate a cohort), clinical eligibility criteria 102. The clinical eligibility criteria may comprise a list of terms, phrases, or values that define subjects' eligibility within the cohort. The system 100 encodes the eligibility criteria in a way that is usable by retrieval module 108, which finds matching subjects and generates snippets for those matching subjects. For example, the encoding may include looking up a list of surface forms 106 (e.g., synonyms or terms with the same or closely related meaning) of each criteria in a knowledge base 103 (e.g., a medical ontology) and collecting each criterion and its surface forms into an unordered set.

The retrieval module 108 identifies candidate subjects using an index of the subjects' documents (e.g., stored in medical records database 104). In some embodiments, the retrieval is performed using a sparse inverted index provided by Elasticsearch. In some embodiments, a neural network based retrieval architecture is used.

A ranking module 110 uses the documents of the candidate subjects (or, more particularly, snippets from the documents) to rank the subjects (into a ranking 112) based on the estimated relevance to the user-specified criteria. As described in more detail below, ranking module 110 estimates relevance using a machine learning model that encodes both the eligibility criteria and appropriate (i.e., matching) portions of the subjects' documents, which are combined to produce estimated relevance scores. In some circumstances, the encodings and the method for computing the relevance score are created by training a machine learning model on noisy/incomplete data without affecting the ranking.

A selection module 114 then selects candidate subjects to present to the user based on the ranking 112. In some embodiments, the selection module 114 uses a calibration process that identifies a stratified subsample of the subjects to label using a lightweight curation process, in which human reviewers inspect short snippets of text to determine whether these subjects truly satisfy the user-specified eligibility criteria. In this manner, a calibration curve, such as that shown in FIG. 3, can be established and used to select an appropriate number of subjects to return to the user.

Figure 2:
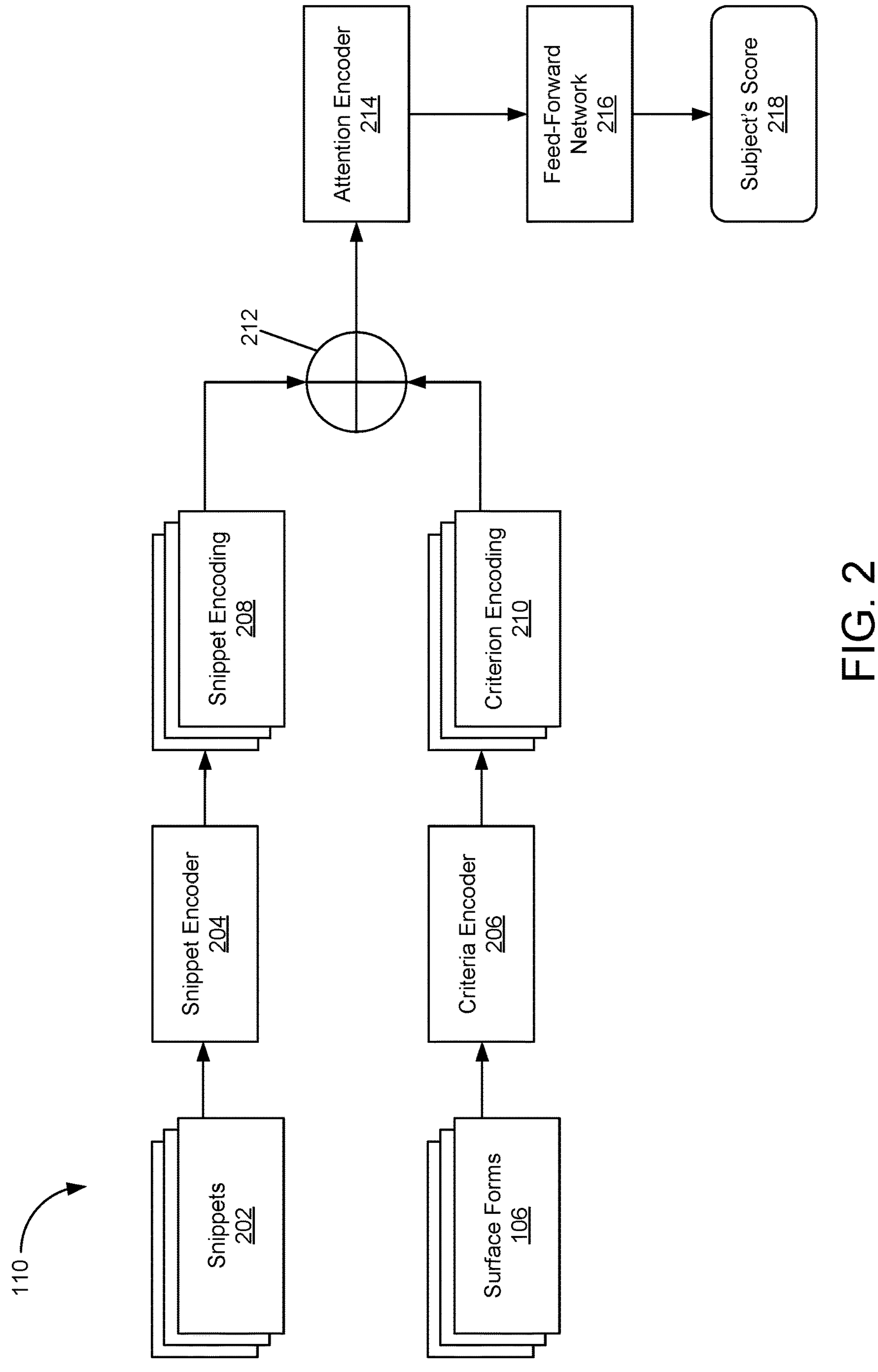
FIG. 2 is a schematic diagram of a ranking module for ranking subjects based on their relevance to clinical eligibility criteria for inclusion within a cohort, in accordance with some embodiments.

FIG. 2 is a schematic diagram of a ranking module 110 for ranking subjects based on their relevance to clinical eligibility criteria for inclusion within a cohort, in accordance with some embodiments. In particular, FIG. 2 illustrates a two-tower architecture for ranking subjects. A snippet encoder 204 receives snippets 202 (e.g., portions of documents in subjects' medical records) from retrieval module 108 (FIG. 1). In some embodiments, the snippets include unstructured text (e.g., text from chart notes entered by a healthcare provider). In some embodiments, the snippets are portions of documents in subjects' medical records that include an instance of a user-specified criterion or one of its surface forms. In some embodiments, the portion includes a predefined amount of text (e.g., 100 words or 100 characters) before and/or after the instance of the user-specified criteria. In some embodiments, the text to be included in the snippet is determined by one or more machine learning algorithms (e.g., neural networks) that identify contextual significance in surrounding words to the surface form. The text includes in the snippet is, in such embodiments, the text that includes the textual significance. In some embodiments, each snippet is individually encoded by snippet encoder 204, thus resulting in a plurality of snippet encodings 208.

Similarly, the ranking module 110 includes a criteria encoder 206 which receives criteria and their surface forms. In some embodiments, each criteria and its surface forms (which, as noted above, may form an unordered set) is separately encoded. Thus, in some circumstances, a plurality of criteria are encoded by criteria encoder 206 into a plurality of criteria encodings 210.

The snippet encodings 208 and the criteria encodings 210 are then concatenated by concatenation module 212. In particular, in some embodiments, an encoding for a snippet that includes an instance of a respective criterion is concatenated with the corresponding encoding for that criterion. These concatenated encodings are fed to an attention encoder 214 that produces a single encoding representing the subject with respect to the set of clinical eligibility criteria. The single encoding representing the subject with respect to the set of clinical eligibility criteria is then passed to a feed-forward network 216 that produces a score for the subject's relevance with respect to the set of clinical eligibility criteria. The subjects are then ranked and selected based on their respective scores.

In some embodiments, snippet encoder 204, criteria encoder 206, attention encoder 214, and feed-forward network 216 are jointly trained machine-learning modules (e.g., neural networks).

FIGS. 1-2 represent just one example of an architecture for implementing the present invention. One of skill in the art, having the benefit of this disclosure, will appreciate that the architecture described above may be modified in various ways without deviating from the spirit of the invention.

Figure 3:
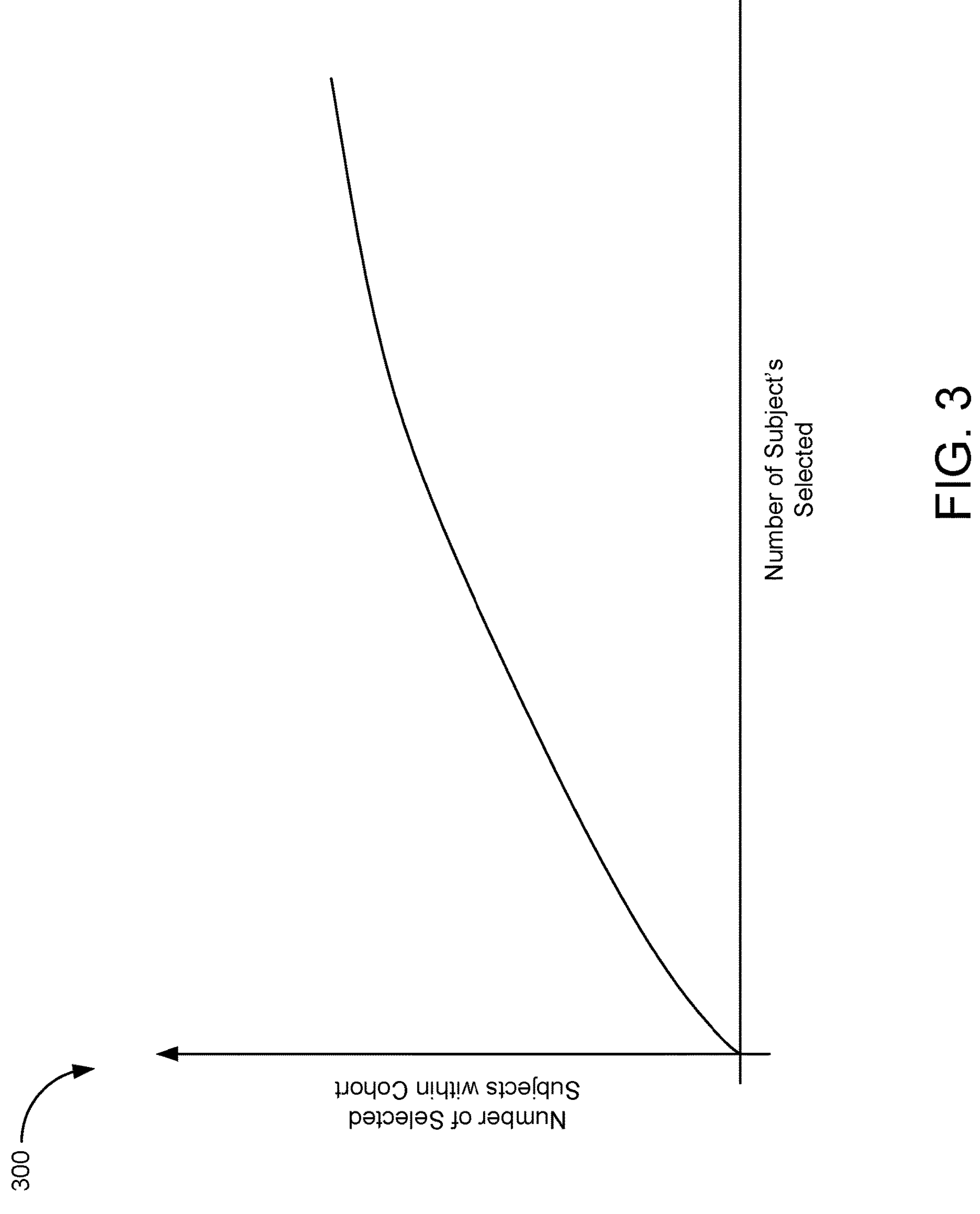
FIG. 3 is a prophetic example of a calibration curve, in accordance with some embodiments.

FIG. 3 is a prophetic example of a calibration curve 300, in accordance with some embodiments. The horizontal axis of the calibration curve 300 represents the number of subjects selected (e.g., by selection module 114, FIG. 1, or during selection operation 426, FIG. 4C). The vertical axis of the calibration curve 300 represents the number of the selected subjects that are within the cohort (i.e., the number of "true positives"). Calibration curve 300 may be generated using a small number of labeled medical records (e.g., small as compared to the number of subjects within the medical records database 104, FIG. 1), wherein the labeled records identify whether the corresponding subjects meet the user-defined eligibility criteria. Note that this labeling is distinct from labeling used to train the model, which is generally trained on criteria that are different from the user-defined eligibility criteria. As such, the labeling used to generate calibration curve 300 is generally performed after the model has been trained, e.g., as part of calibration during use of the model. Statistical methods can be used to generate calibration curve 300 by considering, for example, how many labeled positives (i.e., subjects labeled as falling within the user-specified criteria) and negatives (i.e., subjects labeled as falling within the user-specified criteria) fall within different bins of rankings (e.g., each decade of ranking). The calibration curve 300 can then be used to return an appropriate number of subjects to the user (e.g., as described with respect to operation 428, FIG. 4C).

Figure 4A:
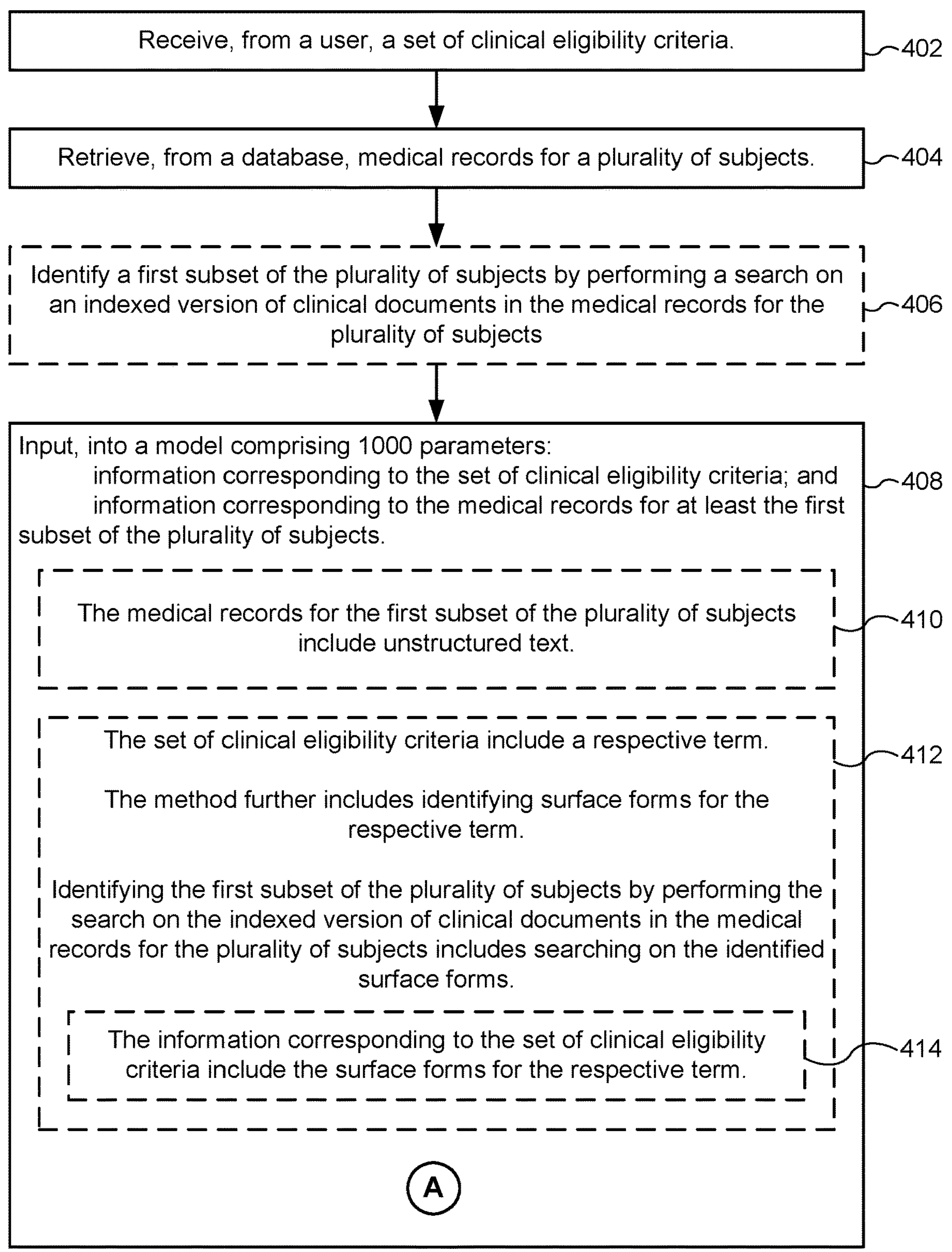
FIGS. 4A-4C illustrate a flowchart for a method of determining a cohort for a study, in accordance with some embodiments.
Figure 4B:
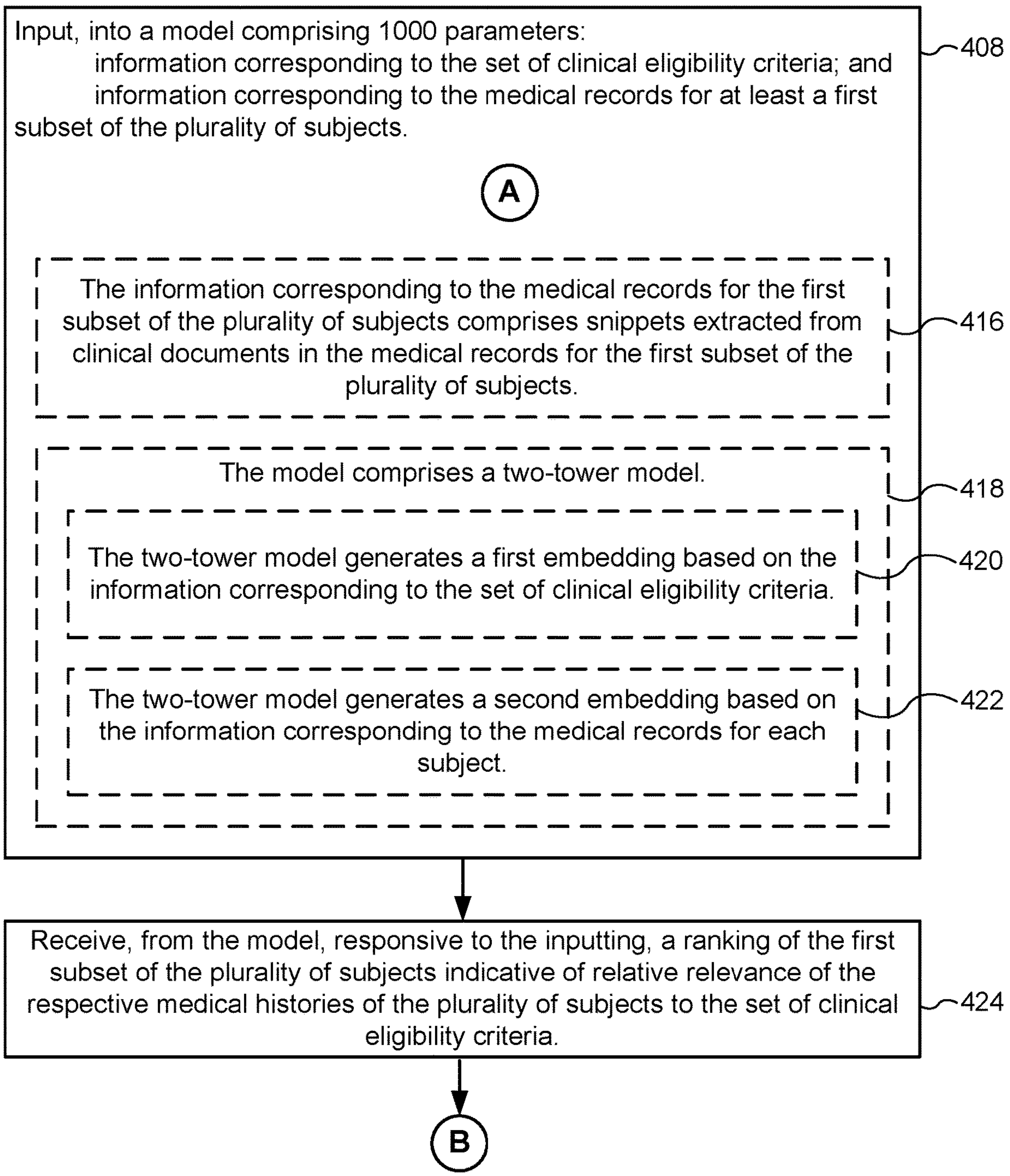
Figure 4C:
Figure 4C:
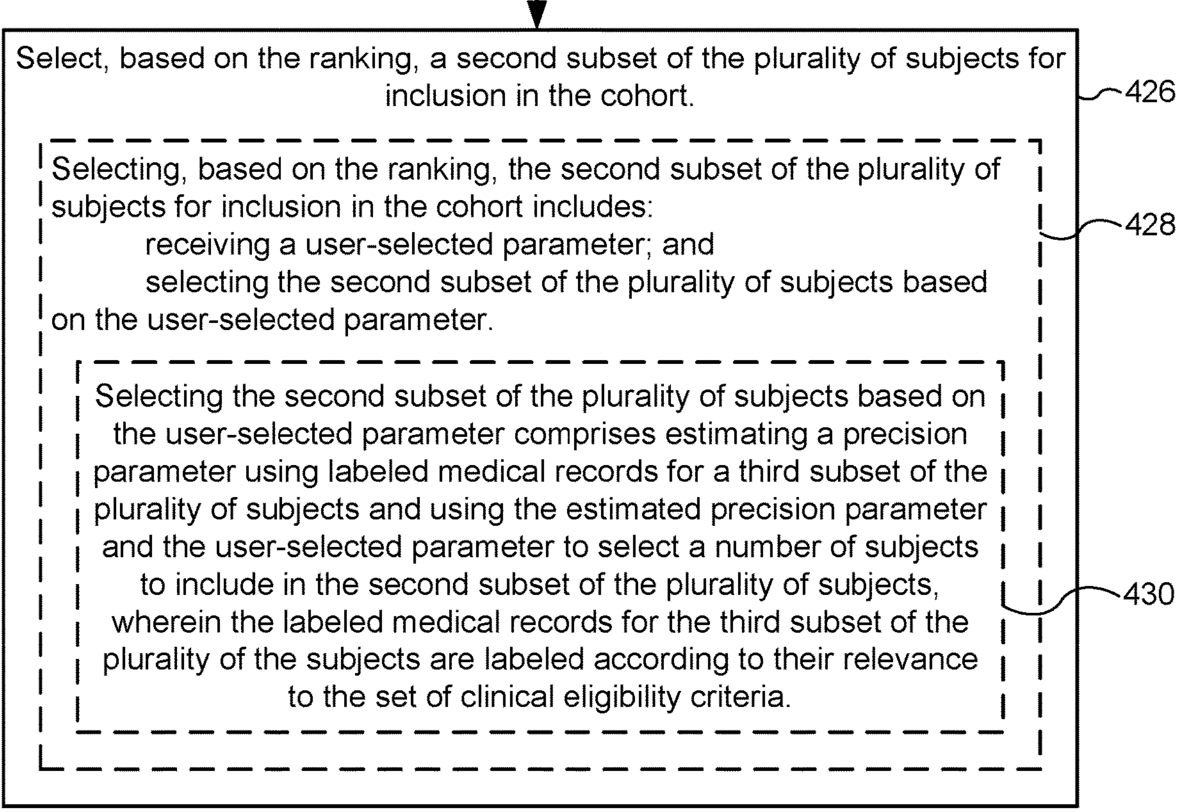

FIGS. 4A-4C illustrate a flowchart for a method 400 of determining a cohort for a study (e.g., generating candidates for inclusion into the cohort based on clinical eligibility criteria), in accordance with some embodiments. The method is performed by a computer system comprising one or more processors and memory (e.g., computer system 500, FIG. 5). Method 400 can be used any time a cohort of subjects is required (e.g., for a clinical trial, a retrospective study, or a prospective study). As described in greater detail below, method 400 uses a model trained to access and/or rank subjects (e.g., patients) according to clinical eligibility criteria. The output of the model is a set (e.g., list) of subjects who are much more likely than the general population to meet the clinical eligibility criteria. Note that, as described below, in some circumstances, the output of the model will not have 100% precision, and thus the output should be viewed as producing candidates for inclusion into the cohort (e.g., with a high, or in some cases user-definable, degree of discriminations/precision).

One of skill in the art, having the benefit of this disclosure, will recognize that method 400 is not a process that could be, or would be, performed by a human. Rather, in a conventional process for cohort generation, a human would perform a computerized database search of medical records (e.g., electronic health records) using various search terms. The search may return results based on the topical relevance of the search terms in medical records (e.g., how often those terms appear), but will not include information with respect to the relevance of the subject (e.g., the patient) to clinical eligibility criteria, and more particularly, will not include a ranking of subjects with respect to the clinical eligibility criteria. Consider, as an example, a researcher who hopes to produce a cohort of subjects who have suffered myocardial infarctions (heart attacks). The research may search medical records for "myocardial infarction," but would then have to wade through numerous results for patients with notes describing a family history of heart attacks, but no personal history of heart attacks. The researcher would have no need to rank the subjects based on their relevance to the clinical eligibility criteria, as described below, because he or she would simply categorize the subjects as relevant (or not) to the clinical eligibility criteria, albeit through a time-consuming and tedious process.

As such, method 400 represents a technological improvement in the search and retrieval of candidates for inclusion within a cohort (e.g., by increasing the discrimination of results).

To that end, method 400 includes, at operation 402, receiving, from a user (e.g., via a user interface of a computer system), a set of clinical eligibility criteria. In some embodiments, the set of clinical eligibility criteria include a plurality of criteria (e.g., 2, 5, or 10 criteria). In some embodiments, the set of clinical eligibility criteria include a single criterion. In some embodiments, each criterion of the set of clinical eligibility criteria is a term (e.g., "PARP inhibitors" or "COVID toe." In some embodiments, the clinical eligibility criteria are objective (binary) criteria defining whether a particular subject is a member of the cohort. In some embodiments, the set of clinical eligibility criteria include inclusion criteria. In some embodiments, the set of clinical eligibility criteria include exclusion criteria.

Method 400 includes, at operation 404, retrieving, from a database, medical records (electronic health records) for a plurality of subjects (e.g., patients). In some embodiments, the database includes medical records for at least 500, 1000, 5000 or 10,000 subjects.

In some embodiments, method 400 includes, at operation 406, identifying a first subset of the plurality of subjects by performing a search on an indexed version of clinical documents in the medical records for the plurality of subjects.

Method 400 includes, at operation 408, inputting, into a model comprising 1000 parameters (e.g., a plurality of parameters): information corresponding to the set of clinical eligibility criteria; and information corresponding to the medical records for at least the first subset of the plurality of subjects. In some embodiments, the model comprises one or more neural networks. In some embodiments, the one or more neural networks include a plurality of encoders and/or modules, discussed in more detail below, that are trained jointly. In some embodiments the medical records for the first subset of the plurality of subjects include (410) unstructured text (e.g., chart notes in an electronic health record (EHR) or other free-form text, e.g., written by a human such as a doctor).

As used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, bias, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1{,}000$; $n \geq 2{,}000$; $n \geq 4{,}000$; $n \geq 5{,}000$; $n \geq 7{,}500$; $n \geq 10{,}000$; $n \geq 20{,}000$; $n \geq 40{,}000$; $n \geq 75{,}000$; $n \geq 100$, 000; n≥200,000; n≥500,000, $n \geq 1 \times 10^6$, $n \geq 5 \times 10^6$, or $n \geq 1 \times 10^7$. As such, the algorithms, models, regressors, and/or classifiers of the present disclosure cannot be mentally performed. In some embodiments n is between 10,000 and $1 \times 10^7$, between 100,000 and $5 \times 10^6$, or between 500,000 and $1 \times 10^6$. In some embodiments, the algorithms, models, regressors, and/or classifier of the present disclosure operate in a k-dimensional space, where k is a positive integer of 5 or greater (e.g., 5, 6, 7, 8, 9, 10, etc.). As such, the algorithms, models, regressors, and/or classifiers of the present disclosure cannot be mentally performed.

In some embodiments, the set of clinical eligibility criteria include a respective term (ref 412). Method 400 further includes identifying surface forms for the respective term (e.g., synonyms and/or phrases that have the same or similar meaning to the respective term, as well as plural and/or singular versions of the respective terms and their surface forms). Identifying the first subset of the plurality of subjects by performing the search on the indexed version of clinical documents in the medical records for the plurality of subjects (see operation 406) includes searching on the identified surface forms.

In some embodiments, the information corresponding to the set of clinical eligibility criteria comprises (e.g., is encoded as) a list of terms (e.g., the specified criteria) and their surface forms (e.g., synonyms). In some circumstances, the surface forms are determined by a knowledge base/ontology (e.g., the Uniform Medical Language System (UMLS), the National Cancer Institute (NCI) thesaurus, etc.). In other circumstances, e.g., in which a knowledge base is unlikely to have an entry for a unique criterion, the user may manually curate the list of surface forms. For example, looking for subjects who experienced an "itchy toe," the user might encode the criterion as ["itchy toe", "itchy big toe", "toe irritation"]. A knowledge base could be used to create this surface form list, but it is unlikely that a knowledge base would have an entry for "itchy toe," so in this case, the list of surface forms is constructed manually. In some embodiments, surface forms of surface forms (e.g., synonyms of synonyms) are also used, and considered surface forms of the original term.

In some embodiments, the information corresponding to the set of clinical eligibility criteria include the surface forms for the respective term (ref 414). Stated another way, in some embodiments, the surface forms are used for both the retrieval operation 406 as well as inputs into the model for ranking subjects.

The information corresponding to the medical records for the first subset of the plurality of subjects (which is passed to the model for ranking subjects) comprises snippets extracted from clinical documents in the medical records for the first subset of the plurality of subjects (ref 416). In some embodiments, each snippet is a portion, less than a whole, of a document. In some embodiments, each snippet is a portion surrounding an instance of a criterion or a corresponding surface form (e.g., a predefined number of words or characters before and/or after the instance of the criterion or the corresponding surface form). For example, if a criterion includes the term "PARP inhibitor," and a respective document includes the sentence "PARP inhibitors may be used in the treatment of breast cancer and ovarian cancer," the system will extract 100 words before and after the term "PARP inhibitor" to produce a single snippet.

In some embodiments, the model comprises a two-tower model (ref 418). In some embodiments, the two-tower model generates, at operation 420, a first embedding (e.g., vector) based on the information corresponding to the set of clinical eligibility criteria. In some embodiments, the two-tower model generates, at operation 422, a second embedding (e.g., vector) based on the information corresponding to the medical records for each subject. In some embodiments, the model includes a first encoder for generating the first embedding based on the information corresponding to the set of clinical eligibility criteria and a second encoder for generating the second embedding based on the information corresponding to the medical records for each subject (e.g., the first encoder receives, as an input, the information corresponding to the set of clinical eligibility criteria (e.g., the criteria and their surface forms) and outputs the first embedding; and the second encoder receives, as an input, the information corresponding to the medical records for each subject (e.g., the snippets) and outputs the second embedding). In some embodiments, the first encoder and the second encoder are trained jointly. In some embodiments, the second encoder generates a separate second embedding for each snippet. The separate second embedding for each snippet is concatenated with the first embedding representing the set of clinical eligibility criteria, resulting in a plurality of embeddings for the subject. The plurality of embeddings for the subject are then fed to an attention encoder that produces a single encoding representing the subject with respect to the set of clinical eligibility criteria. The single encoding representing the subject with respect to the set of clinical eligibility criteria is then passed to a scoring module (e.g., a feed-forward network) that produces a score for the subject's relevance with respect to the set of clinical eligibility criteria. The score is then used to rank the subjects with respect to the set of clinical eligibility criteria. In some embodiments, the attention encoder and the scoring module are jointly trained with the first encoder and the second encoder. In various embodiments, any of the first encoder, second encoder, attention encoder, or scoring module comprises a neural network.

In some embodiments, method 400 includes training the model using a set of labeled training documents and a set of training criteria. Each labeled training document comprises a document in a respective subject's medical records and a label indicating relevance (e.g., binary relevance) of the subject's medical history to the respective criteria of the set of training criteria. In many circumstances, the set of training criteria is distinct from (e.g., and non-overlapping with) the set of clinical eligibility criteria. In some embodiments, the set of clinical eligibility criteria include at least one criterion that is not included in the set of training criteria (e.g., the model is not trained to categorize on specific criteria, but is rather trained to categorize on any user-defined criteria). In other words, the model is a general machine trained to rank subjects with respect to criteria that it was not trained on (e.g., criteria defined by a user after the model has already been trained). Thus, in some embodiments, method 400 comprises training the model before receiving the set of clinical eligibility criteria.

In some embodiments the labels include false negatives (e.g., the label erroneously indicates that the subject's medical history is not relevant to the respective criteria). In some embodiments, the ranking is independent of false negatives used to train the model.

In some embodiments, the set of labeled training documents includes non-trivial negative documents for a respective training criterion of the set of training criteria, wherein each non-trivial negative document comprises a document that includes the respective training criterion or a surface form of the respective training criterion but is not relevant to the respective training criterion. Various non-limiting examples of non-trivial negative documents are as follows: (1) a document in the subject's medical records that mentions a family history of a certain condition, but the subject has not been diagnosed with the condition and thus would not be included in a cohort of subjects who have had the condition; (2) a document in the subject's medical records that includes a mention of a particular treatment ("PARP inhibitors may be used in the treatment of breast cancer and ovarian cancer") but does not indicate that the subject has received the treatment and thus the subject would not be included in a cohort of subjects who have received the treatment; (3) a document in the subject's medical records that reports all of the mutations tested in a particular assay, but does not indicate that the subject's sample included a certain mutation, and thus the subject would not be included in a cohort of subjects who have had the certain mutation. In contrast, a positive document is a document that indicates that the subject is a member of the cohort (e.g., a document in the subject's medical records identifies a personal history of a certain condition or records the certain condition as a diagnosis, and thus the subject is included in a cohort of subjects who have had the certain condition).

Method 400 includes receiving, at operation 424, from the model, responsive to the inputting, a ranking of the first subset of the plurality of subjects indicative of relative relevance of the respective medical histories of the plurality of subjects to the set of clinical eligibility criteria. Note that, although the model evaluates the subjects' medical records (e.g., documents within the subjects' medical records), the model determines (e.g., outputs) relevance of the subject, not the individual records, to the set of clinical eligibility criteria. For example, the user may wish to identify a cohort of subjects that underwent a certain procedure, received a certain diagnosis, received a certain medication/treatment, had a certain biomarker and/or experienced certain adverse effects. The model ranks subjects by a likelihood that individual subjects meet these eligibility criteria, rather than merely identifying the relevance of documents in the subjects' medical histories.

Method 400 includes selecting, at operation 426, based on the ranking, a second subset of the plurality of subjects for inclusion in the cohort. In some embodiments, the second subset of the plurality of subjects comprises candidates for inclusion in the cohort (e.g., which may then be evaluated by a human in order to produce a final cohort).

In some embodiments, selecting, based on the ranking, the second subset of the plurality of subjects for inclusion in the cohort includes: receiving a user-selected parameter; and selecting the second subset of the plurality of subjects based on the user-selected parameter (ref 428). In some embodiments, the user-selected parameter is a precision parameter. For example the user may specify that the system should return results that contain at least 50% "true positives" (e.g., 50% of the subjects returned are truly in the cohort). In some embodiments, the system responds by selecting, as the second subset of the plurality of subjects for inclusion in the cohort, as many of the top-ranked subjects as allowable given the need for the precision parameter to hold true (e.g., using calibration data, described below). If, for example, using a calibration curve (e.g., FIG. 3), the system determines that it can return 1000 subjects with a true positive rate of 50%, but that returning any more subjects would result in a true positive rate of less than 50%, the system will return 1000 subjects. In some embodiments, the user-selected parameter is a desired number of true positives. For example, the user may specify that she needs approximately 500 subjects for a study. The system then responds by using calibration data to determine how many subjects it needs to return in order to produce 500 true positives (e.g., the system will return 1000 subjects if the precision for returning 500 true positives is 50%). The user may then manually sort the remaining results, which of course have a much higher degree of discrimination, to produce her actual cohort.

In some embodiments, selecting the second subset of the plurality of subjects based on the user-selected parameter comprises estimating a precision parameter using labeled medical records for a third subset of the plurality of subjects and using the estimated precision parameter and the user-selected parameter to select a number of subjects to include in the second subset of the plurality of subjects, wherein the labeled medical records for the third subset of the plurality of the subjects are labeled according to their relevance to the set of clinical eligibility criteria (ref 430). For example, the third subset of the plurality of subjects consist of less than all of the plurality of subjects, and, in some cases, much less than all of the plurality of subjects. For example, the database may contain records for thousands or tens of thousands of subjects, 100 of which are manually labelled according to their relevance to the set of clinical eligibility criteria (e.g., labeled as true positives). In some embodiments, estimating the precision parameter comprises generating, using the manual labeling of the third subset of the plurality of subjects, the number of true positives versus the number of returned results. In some embodiments, the precision parameter is the ratio of the true positives versus the number of returned results.

In various embodiments, the selection of the second subset of the plurality of subjects is used for any of a variety of downstream purposes. As one example, in some embodiments, method 400 adding structured data to a subject's records indicating that the subject meets the criteria for the cohort. For example, the added structured data may indicate whether the subject meets an individual criterion in the set of criteria (e.g., the presence of the term, phrase, or value that is being searched for). Alternatively, or in addition, the added structured data indicates that the subject meets all of the criteria for inclusion in the cohort (e.g., the added structured data is a cohort-inclusion indicium). Such structured data can then be used to return results using traditional structured searches. More particularly, in some embodiments, method 400 includes adding structured data to an electronic health record of a respective subject in the second subset of subjects, wherein the structured data indicates that the respective subject is a member of the cohort and/or meets particular criteria in the set of criteria. In some embodiments, method 400 includes, after adding the structured data, receiving a structured query for subjects in the cohort and/or who meet the particular criteria and, in response to receiving the structured query, returning the respective subject based on the structured data added to the respective subject's electronic health record.

In some embodiments, the added structured data indicates a record (e.g., document or snippet) which met the particular criteria. In some embodiments, the added structured data indicates a time within the record at which the particular criteria were met. In some embodiments, these data may be searched for (e.g., using a structured query) and/or returned as part of the results of a query.

In some embodiments, the added structured data includes an optional indication of any determinations that a respective subject did not meet particular criteria of the set of criteria.

As another example, in some embodiments, method 400 includes, based on a determination that a respective subject in the second subset of subjects meets the criteria for inclusion in the cohort, identifying a risk of a potential disease state of the respective subject. In some embodiments, method 400 includes notifying the subject or their healthcare provider of the risk.

In some embodiments, the method 400 includes identify a treatment (e.g., a new treatment) available to the cohort of subjects and notifying the respective subject in the second subset of subjects that the treatment (e.g., for an ongoing diagnosis) may be available.

In some embodiments, the method 400 identifying one or more clinical trials available to the cohort of subjects and notifying a respective subject in the second subset of subjects that the new clinical trials for an ongoing diagnosis may be available.

In some embodiments, the method 400 includes identifying a third-party (e.g., a pharmaceutical company) that a number of members of the cohort may be viable subjects for a clinical trial.

Figure 5:
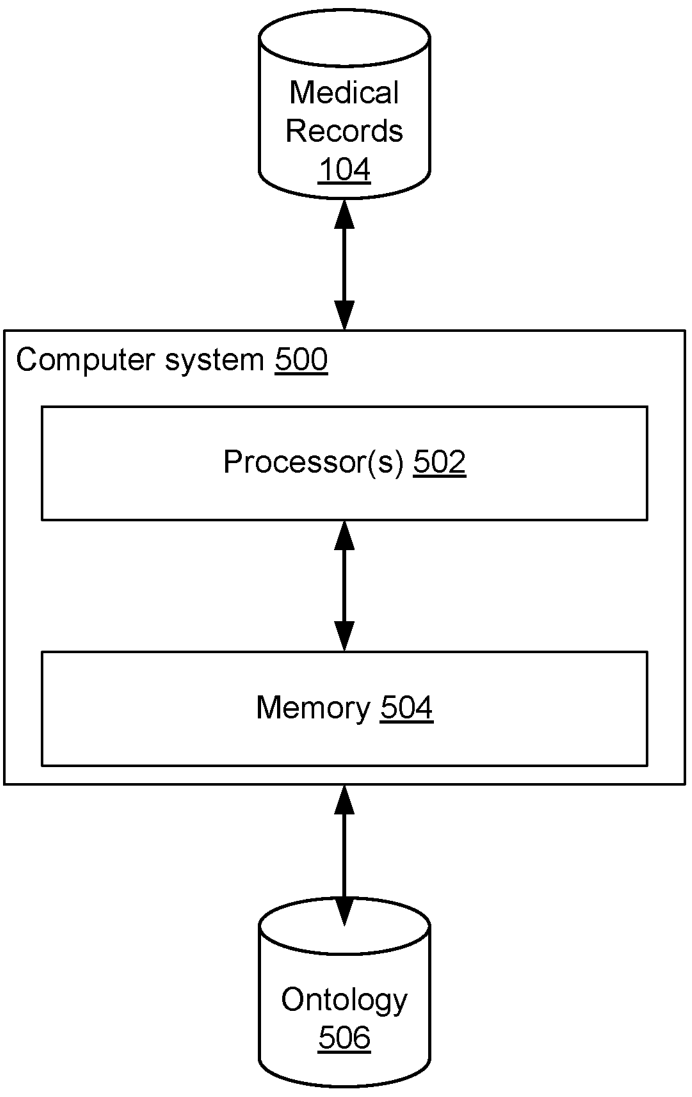
FIG. 5 is a schematic diagram of a computer system for determining a cohort for a study, in accordance with some embodiments.

FIG. 5 is a schematic diagram of a computer system 500 for determining a cohort for a study, in accordance with some embodiments. The computer system 500 includes one or more processors 502 (e.g., central processing units and/or cores) and memory 504 storing programs for execution by the one or more processors 502.

Memory 504 includes high-speed random-access memory, such as DRAM, SRAM, DDR RAM, or other random-access solid-state memory devices; and may include non-volatile memory, such as one or more magnetic disk storage devices, optical disk storage devices, flash memory devices, or other non-volatile solid-state storage devices. Memory 504 may optionally include one or more storage devices remotely located from the processors 502. Memory 504, or alternately, the non-volatile memory solid-state storage devices within memory 504, includes a non-transitory computer-readable storage medium. In some embodiments, memory 504 stores one or more programs that include instructions for performing the methods described herein (e.g., method 400, FIGS. 4A-4C).

In some embodiments, computer system 500 is in communication with one or more medical records databases 104 (an electronic database). The medical records database 104 stores and provides medical records (electronic health records) for subjects (e.g., patients), including medical documents that form a portion of the electronic health records. Such medical documents may include unstructured text, such as healthcare providers' chart notes. In some embodiments, the medical records database is internal to computer system 500.

In some embodiments, computer system 500 is in communication with or more ontology databases 506 storing medical ontologies/thesauruses (also referred to as knowledge bases) that are used to generate surface forms of terms that establish clinical eligibility criteria in a cohort. Examples of such ontologies are the Uniform Medical Language System (UMLS), the National Cancer Institute (NCI) thesaurus, etc. In some embodiments, computer system 500 uses an internally developed ontology, which is stored in a database and/or memory internal to computer system 500.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles and their practical applications, to thereby enable others skilled in the art to best utilize the embodiments and various embodiments with various modifications as are suited to the particular use contemplated.

What is claimed is:

1. A method, by one or more processing devices, of determining a cohort for a clinical trial, comprising:

receiving, from a user, a set of clinical eligibility criteria;

generating a plurality of surface forms comprising, for each respective clinical eligibility criterion in the set of clinical eligibility criteria, a corresponding set of surface forms for the respective clinical eligibility criterion;

retrieving, from a database, medical records for a plurality of subjects comprising unstructured text from clinical documents;

extracting a plurality of sets of snippets comprising, for each respective subject in a first subset of the plurality of subjects, a corresponding set of snippets comprising unstructured text from a corresponding clinical document for the respective subject;

inputting the plurality of surface forms into a first encoder and generating, by the first encoder, criterion embeddings;

inputting, for each respective subject in the first subset of the plurality of subjects, the corresponding set of snippets into a second encoder and generating, by the second encoder, corresponding snippet embeddings;

inputting, for each respective subject in the first subset of the plurality of subjects, the criterion embeddings and the corresponding snippet embeddings for the respective subject, into a third encoder comprising an attention mechanism and generating, by the third encoder, a corresponding joint embedding representing the corresponding snippet embeddings in the context of the criterion embeddings;

generating a plurality of relevance scores for inclusion in the clinical trial by inputting, for each respective subject in the first subset of the plurality of subjects, the corresponding joint embedding into a scoring model and generating, by the scoring model, a corresponding relevance score for inclusion of the respective subject in the clinical trial, wherein the scoring model was trained against a set of training criteria that are different than the set of clinical eligibility criteria; and selecting, based on the plurality of relevance scores a second subset of the plurality of subjects for inclusion in the cohort.

2. The method of claim 1, further comprising:

identifying the first subset of the plurality of subjects by performing a search on an indexed version of clinical documents in the medical records for the plurality of subjects.

3. The method of claim 2, wherein:

identifying the first subset of the plurality of subjects by performing the search on the indexed version of clinical documents in the medical records for the plurality of subjects includes searching on the generated plurality of surface forms.

4. The method of claim 1, further comprising training the model using a set of labeled training documents and the set of training criteria, each respective labeled training document in the set of labeled training documents comprising a document in a respective subject's medical records and a corresponding label indicating relevance of the subject's medical history to the set of training criteria.

5. The method of claim 4, wherein at least one corresponding label is a false negative.

6. The method of claim 4, wherein the set of labeled training documents includes non-trivial negative documents for a respective training criterion of the set of training criteria, wherein each non-trivial negative document comprises a document that includes the respective training criterion or a surface form of the respective training criterion but is not relevant to the respective training criterion.

7. The method of claim 1, wherein selecting, based on the plurality of relevance scores, the second subset of the plurality of subjects for inclusion in the cohort includes:

receiving a user-selected parameter; and selecting the second subset of the plurality of subjects based on the user-selected parameter.

8. The method of claim 7, wherein selecting the second subset of the plurality of subjects based on the user-selected parameter comprises estimating a precision parameter using labeled medical records for a third subset of the plurality of subjects and using the estimated precision parameter and the user-selected parameter to select a number of subjects to include in the second subset of the plurality of subjects, wherein the labeled medical records for the third subset of the plurality of the subjects are labeled according to their relevance to the set of clinical eligibility criteria.

9. The method of claim 1, further comprising:

adding structured data to an electronic health record of a respective subject in the second subset of the plurality of subjects, wherein the structured data indicates that the respective subject meets one or more respective criterion of the set of clinical trial eligibility criteria;

after adding the structured data, receiving a structured query for subjects who meet the one or more respective criterion of the set of clinical trial eligibility criteria; and, in response to receiving the structured query, returning the respective subject based on the structured data added to the respective subject's electronic health record.

10. A computer system, comprising:

one or more processors; and memory storing one or more programs, the one or more programs including instructions for:

receiving, from a user, a set of clinical eligibility criteria;

generating a plurality of surface forms comprising, for each respective clinical eligibility criterion in the set of clinical eligibility criteria, a corresponding set of surface forms for the respective clinical eligibility criterion;

retrieving, from a database, medical records for a plurality of subjects comprising unstructured text from clinical documents;

extracting a plurality of sets of snippets comprising, for each respective subject in a first subset of the plurality of subjects, a corresponding set of snippets comprising unstructured text from a corresponding clinical document for the respective subject;

inputting the plurality of surface forms into a first encoder and generating, by the first encoder, criterion embeddings;

inputting, for each respective subject in the first subset of the plurality of subjects, the corresponding set of snippets into a second encoder and generating, by the second encoder, corresponding snippet embeddings;

inputting, for each respective subject in the first subset of the plurality of subjects, the criterion embeddings and the corresponding snippet embeddings for the respective subject, into a third encoder comprising an attention mechanism and generating, by the third encoder, a corresponding joint embedding representing the corresponding snippet embeddings in the context of the criterion embeddings;

generating a plurality of relevance scores for inclusion in the clinical trial by inputting, for each respective subject in the first subset of the plurality of subjects, the corresponding joint embedding into a scoring model and generating, by the scoring model, a corresponding relevance score for inclusion of the respective subject in the clinical trial, wherein the scoring model was trained against a set of training criteria that are different than the set of clinical eligibility criteria; and selecting, based on the plurality of relevance scores a second subset of the plurality of subjects for inclusion in the cohort.

11. The computer system of claim 10, wherein the one or more programs include instructions for:

identifying the first subset of the plurality of subjects by performing a search on an indexed version of clinical documents in the medical records for the plurality of subjects.

12. The computer system of claim 11, wherein:

identifying the first subset of the plurality of subjects by performing the search on the indexed version of clinical documents in the medical records for the plurality of subjects includes searching on the generated plurality of surface forms.

13. The computer system of claim 10, wherein the one or more programs include instructions for training the model using a set of labeled training documents and the set of training criteria, each respective labeled training document in the set of labeled training documents comprising a document in a respective subject's medical records and a corresponding label indicating relevance of the subject's medical history to the set of training criteria.

14. The computer system of claim 13, wherein at least one corresponding label is a false negative.

15. The computer system of claim 13, wherein the set of labeled training documents includes non-trivial negative documents for a respective training criterion of the set of training criteria, wherein each non-trivial negative document comprises a document that includes the respective training criterion or a surface form of the respective training criterion but is not relevant to the respective training criterion.

16. The computer system of claim 10, wherein selecting, based on the plurality of relevance scores, the second subset of the plurality of subjects for inclusion in the cohort includes:

receiving a user-selected parameter; and selecting the second subset of the plurality of subjects based on the user-selected parameter.

17. The computer system of claim 16, wherein selecting the second subset of the plurality of subjects based on the user-selected parameter comprises estimating a precision parameter using labeled medical records for a third subset of the plurality of subjects and using the estimated precision parameter and the user-selected parameter to select a number of subjects to include in the second subset of the plurality of subjects, wherein the labeled medical records for the third subset of the plurality of the subjects are labeled according to their relevance to the set of clinical eligibility criteria.

18. A non-transitory computer-readable storage medium storing one or more storing one or more programs for execution by a computer system with one or more processors, the one or more programs including instructions for:

receiving, from a user, a set of clinical eligibility criteria;

generating a plurality of surface forms comprising, for each respective clinical eligibility criterion in the set of clinical eligibility criteria, a corresponding set of surface forms for the respective clinical eligibility criterion;

retrieving, from a database, medical records for a plurality of subjects comprising unstructured text from clinical documents;

extracting a plurality of sets of snippets comprising, for each respective subject in a first subset of the plurality of subjects, a corresponding set of snippets comprising unstructured text from a corresponding clinical document for the respective subject;

inputting the plurality of surface forms into a first encoder and generating, by the first encoder, criterion embeddings;

inputting, for each respective subject in the first subset of the plurality of subjects, the corresponding set of snippets into a second encoder and generating, by the second encoder, corresponding snippet embeddings;

inputting, for each respective subject in the first subset of the plurality of subjects, the criterion embeddings and the corresponding snippet embeddings for the respective subject, into a third encoder comprising an attention mechanism and generating, by the third encoder, a corresponding joint embedding representing the corresponding snippet embeddings in the context of the criterion embeddings;

generating a plurality of relevance scores for inclusion in the clinical trial by inputting, for each respective subject in the first subset of the plurality of subjects, the corresponding joint embedding into a scoring model and generating, by the scoring model, a corresponding relevance score for inclusion of the respective subject in the clinical trial, wherein the scoring model was trained against a set of training criteria that are different than the set of clinical eligibility criteria; and selecting, based on the plurality of relevance scores a second subset of the plurality of subjects for inclusion in the cohort.

* * * * *